US00PP17909P2

(12) United States Plant Patent
Trees

(10) Patent No.: US PP17,909 P2
(45) Date of Patent: Aug. 7, 2007

(54) ***ANGELONIA* PLANT NAMED 'BALANGLADER'**

(50) Latin Name: *Angelonia angustifolia*
Varietal Denomination: Balanglader

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 23 days.

(21) Appl. No.: 11/319,331

(22) Filed: Dec. 28, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2006/0115 filed Jan. 12, 2006.

*Primary Examiner*—Anne Marie Grunberg
*Assistant Examiner*—Annette H Para
(74) *Attorney, Agent, or Firm*—Audrey Charles

(57) ABSTRACT

A new and distinct cultivar of *Angelonia* plant named 'Balanglader' characterized by its lavender-colored flowers, medium-sized flowers, and compact, upright growth habit.

1 Drawing Sheet

Latin name of genus and species of plant claimed: *Angelonia angustifolia.*
Variety denomination: 'Balanglader'.

BACKGROUND OF THE INVENTION

The present invention relates to a new and distinct cultivar of *Angelonia* plant botanically known as *Angelonia angustifolia* and hereinafter referred to by the cultivar name 'Balanglader'.

The new cultivar was developed by the inventor in a controlled breeding program during July 1999 at Arroyo Grande, Calif. The objective of the breeding program was the development of *Angelonia* cultivars with unique flower colors, good branching, and compact growth habit.

The female (seed) parent of the new cultivar was the proprietary *Angelonia angustifolia* breeding selection designated 254-AA, not patented, characterized by its pink-colored flowers with purple-colored spots, dark green-colored foliage, and well-branched, mounded growth habit. The male (pollen) parent of the new cultivar was the proprietary *Angelonia angustifolia* breeding selection designated BFP-272, not patented, characterized by its white-colored flowers, dark green-colored foliage, and well-branched, compact, and upright growth habit. The new cultivar was discovered and selected by the inventor as a single flowering plant within the progeny of the above stated cross-pollination during October 2000 in a controlled environment at Arroyo Grande, Calif.

Asexual reproduction of the new cultivar by terminal stem cuttings since October 2000 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balanglader' as a new and distinct cultivar of *Angelonia* plant:

1. Lavender-colored flowers;
2. Medium-sized flowers; and
3. Compact, upright growth habit.

Plants of the new cultivar differ from plants of the female parent primarily in flower color and growth habit and from plants of the male parent primarily in flower color.

Of the *Angelonia* cultivars known to the inventor, the most similar to 'Balanglader' is the *Angelonia* cultivar 'Balangimla', U.S. Plant Pat. No. 13,922. However, in side-by-side comparisons, plants of the new cultivar differ from plants of 'Balangimla' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balanglader'. The plants were grown in 10 cm pots for 11 weeks in a greenhouse at West Chicago, Ill.

DETAILED BOTANICAL DESCRIPTION

Figure 1:
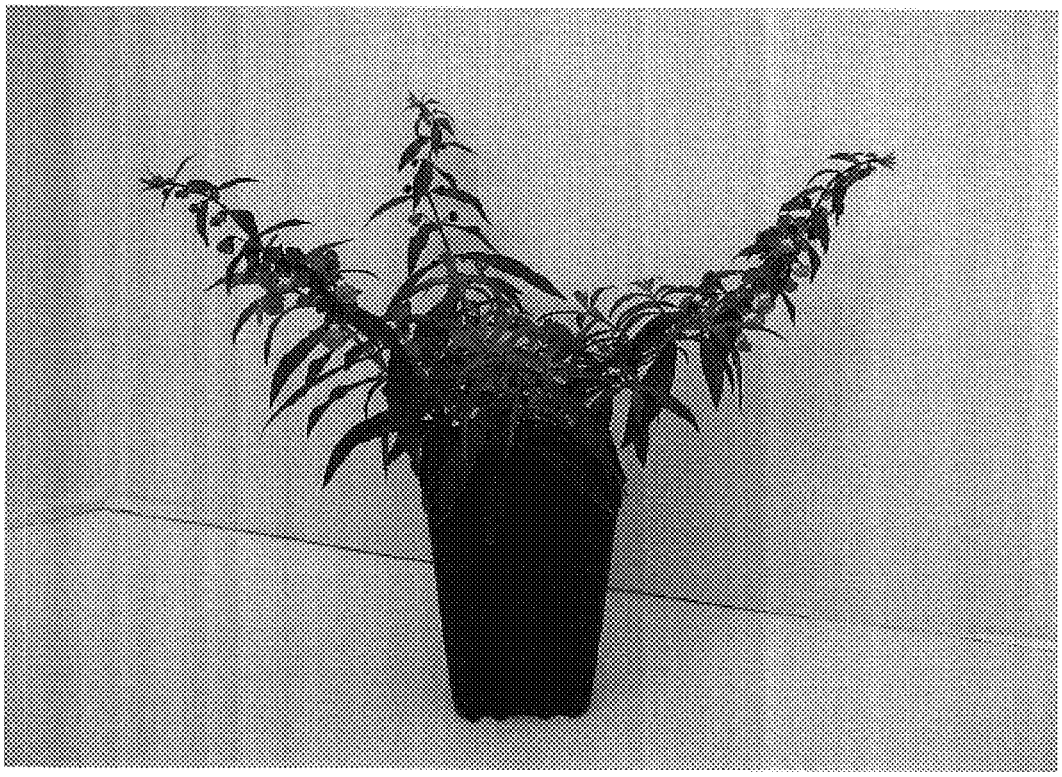
FIG. 1 illustrates a side view of the overall growth and flowering habit of 'Balanglader'.
Figure 2:
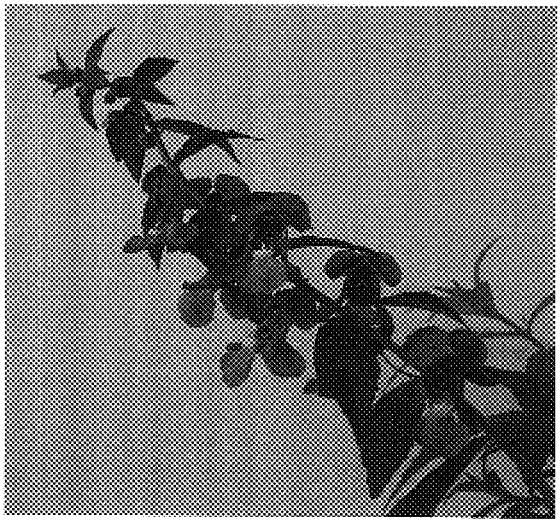
FIG. 2 illustrates a close-up view of a single raceme of 'Balanglader'.
Figure 3:
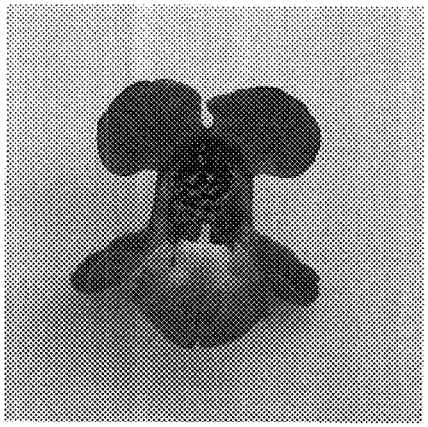
FIG. 3 illustrates a close-up view of an individual flower of 'Balanglader'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Dec. 20, 2005. The readings were taken between 9:00 a.m. and 11:00 a.m. under natural light conditions.

The following descriptions and measurements describe plants produced from cuttings from stock plants and grown in a double polycarbonate-covered greenhouse under conditions comparable to those used in commercial practice. The plants were grown in 10 cm pots for 11 weeks while utilizing a soilless growth medium. Greenhouse temperatures were maintained at approximately 75° F. to 85° F. (24° C. to 29° C.) during the day and approximately 62° F. to 70° F. (17° C. to 21° C.) during the night. Greenhouse light levels were maintained at approximately 6,000 to 10,000 footcandles during the day.

Botanical classification: *Angelonia angustifolia,* cultivar Balanglader.

Parentage:

*Female (seed) parent.*—Proprietary *Angelonia angustifolia* breeding selection designated 254-AA, not patented.

*Male (pollen) parent.*—Proprietary *Angelonia angustifolia* breeding selection BFP-272, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibous.

*Rooting habit.*—Freely branching.

Plant description:

*Crop time.*—Approximately 6 to 7 weeks from a rooted cutting.

*Habit of growth.*—Compact.

*Form.*—Upright, freely branching.

*Size.*—Height (from soil level to top of plant plane): Approximately 17.1 cm. Diameter (area of spread): Approximately 28.0 cm.

*Main branch.*—Quantity per plant: Approximately 5. Shape: Square in cross section. Strength: Moderately strong. Length from soil level to base of raceme: Approximately 11.0 cm. Diameter: Approximately 2.1 mm. Texture: Glabrous. Color: 145A with an overlay of between 183A and 183B. Internode length at center of branch: Approximately 1.8 cm.

*Foliage.*—Quantity of leaves per main branch: Approximately 23. Type: Simple. Fragrance: None. Arrangement: Opposite. Orientation to stem: At right angle. Shape: Oblanceolate. Margin: Serrate. Apex: Acute. Base: Attenuate, sessile. Length of leaf at center of branch: Approximately 6.3 cm. Width of leaf at center of branch: Approximately 1.4 cm. Texture of upper and lower surfaces: Glabrous. Venation pattern: Pinnate. Color of upper surface of mature foliage: 137A with venation of 138D. Color of lower surface of mature foliage: Darker than 138B with venation of 138D.

Flowering description:

*Flowering habit.*—'Balanglader' is freely flowering under outdoor growing conditions with substantially continuous blooming from spring through autumn and year round in greenhouse environment.

*Time to first flower.*—Approximately 12 weeks from sticking of unrooted cutting.

*Lastingness of individual bloom.*—Approximately 7 to 10 days.

*Inflorescence type/description.*—Terminal racemes. Length: Approximately 9.2 cm. Width: Approximately 4.2 cm. Number per plant: Approximately 2 open racemes per plant. Number of fully open flowers per raceme at any one time: Approximately 9.

Flower description:

*Type/fragrance.*—Bilabiate. No fragrance.

*Bud.*—Rate of opening: 3 to 4 days from first color to fully open. Shape: Globular. Length: Approximately 7.4 mm. Diameter: Approximately 5.4 mm. Color of upper surface: 91A. Color of lower surface: 86A.

*Flower size/aspect.*—Length: Approximately 2.2 cm. Width: Approximately 1.7 cm. Depth: Approximately 1.1 cm. Aspect: Facing outward.

*Petals.*—Quantity: 5 per flower, fused at base forming a throat, an upper lip with two petals, and a lower lip with three petals—one central and one lateral on each side.

*Upper lip.*—Petal apex: Emarginate, curling inward. Petal margin: Entire. Length of petals: Approximately 6.0 mm. Width of each petal: Approximately 8.4 mm. Color of upper surface: 92A. Color of lower surface: 92B. Texture of upper surface: Glandular-pubescent at base. Texture of lower surface: Glabrous. Gland color: Colorless, translucent.

*Lower lip, lateral petals.*—Petal apex: Emarginate. Petal margin: Entire, undulate. Length of petals from throat: Approximately 7.4 mm. Width of each petal: Approximately 8.2 mm. Color of upper surface: 92A. Color of lower surface: 92B. Texture of upper surface of petals: Sparsely glandular-pubescent, denser at base. Texture of lower surface of petals: Glandular pubescent. Gland color: Colorless, translucent.

*Lower lip, central petal.*—Petal apex: Emarginate. Petal margin: Entire, undulate. Length of petal from palate: Approximately 6.8 mm. Width of petal: Approximately 9.0 mm. Color of upper surface: 92A. Color of lower surface: 92B fading to 92D at base. Texture of upper surface of petal: Sparsely glandular-pubescent, denser at base. Texture of lower surface of petal: Densely glandular-pubescent. Gland color: Colorless, translucent.

*Throat.*—Length: Approximately 5.2 mm. Width: Approximately 5.8 mm. Texture of inner and outer surfaces: Glabrous. Color of inner surface: N80C with spots of 79A. Color of outer surface: 91A with spots of 79A through 79D. Palate color: 155C with spots of 79A and an overlay of 144C. Palate texture: Sparsely glandular-pubescent. Teeth color: 144C inner surface.

*Pedicel.*—Strength: Good. Length: Approximately 1.0 cm. Diameter: Approximately 0.5 mm. Angle to stem: Acute. Texture: Glabrous. Color: 144A with overlay of 187A.

*Calyx.*—Shape: Five-pointed star, cupped. Width: Approximately 5.0 mm.

*Sepal.*—Quantity per flower: 5. Shape: Lanceolate. Margin: Entire. Apex: Acuminate. Length: Approximately 4.0 mm. Width: Approximately 1.0 mm. Texture of upper and lower surfaces: Glabrous. Color of upper and lower surfaces: 144A with overlay of 187A.

*Reproductive organs.*—Androecium: Stamen quantity: 4 per flower. Stamen length: Approximately 2.0 mm. Filament color: 155C with overlay of 92A. Anther shape: Bilobed. Anther length: Approximately 1.7 mm. Anther color: N92A. Amount of pollen: Abundant. Pollen color: 155D. Gynoecium: Pistil quantity: One per flower. Pistil length: Approximately 4.0 mm. Stigma length: Approximately 0.5 mm. Stigma color: 155C with overlay of 92A. Style length: Approximately 2.3 mm. Style color: 155C with overlay of 92A. Ovary diameter: Approximately 1.2 mm. Ovary texture: Glabrous. Ovary color: 144B with overlay of 183A.

Seed and fruit production: Neither seed not fruit production has been observed.

Disease and pest resistance: Resistance to pathogens and pests common to *Angelonia* has not been observed.

What is claimed is:

1. A new and distinct cultivar of *Angelonia* plant named 'Balanglader', substantially as herein shown and described.

* * * * *